(12) United States Patent
Schweikert et al.

(10) Patent No.: US 10,391,244 B2
(45) Date of Patent: Aug. 27, 2019

(54) USE ACTIVATED EMERGENCY ALERT FOR A MEDICAL DEVICE

(71) Applicants: Katherine Schweikert, Hopkinton, MA (US); Robert J. Schweikert, Hopkinton, MA (US)

(72) Inventors: Katherine Schweikert, Hopkinton, MA (US); Robert J. Schweikert, Hopkinton, MA (US)

( * ) Notice: Subject to any disclaimer, the term of this patent is extended or adjusted under 35 U.S.C. 154(b) by 582 days.

(21) Appl. No.: 14/986,812

(22) Filed: Jan. 4, 2016

(65) Prior Publication Data

US 2016/0193408 A1 Jul. 7, 2016

Related U.S. Application Data

(60) Provisional application No. 62/124,753, filed on Jan. 2, 2015.

(51) Int. Cl.
| | |
|---|---|
| *A61M 5/178* | (2006.01) |
| *G08B 25/01* | (2006.01) |
| *G08B 25/00* | (2006.01) |
| *A61M 5/20* | (2006.01) |
| *A61M 5/50* | (2006.01) |

(52) U.S. Cl.
CPC .......... *A61M 5/178* (2013.01); *G08B 25/016* (2013.01); *A61M 5/20* (2013.01); *A61M 5/50* (2013.01); *G08B 25/009* (2013.01)

(58) Field of Classification Search
CPC .......... A61M 5/178; A61M 5/20; A61M 5/31; A61M 5/3157; A61M 5/50; A61M 2205/0227; A61M 2205/18; A61M 2205/3553; A61M 2205/3576; A61M 2205/3584; A61M 2205/3592; A61M 2205/6027; A61M 2205/6036; G08B 25/009; G08B 25/016
See application file for complete search history.

(56) References Cited

U.S. PATENT DOCUMENTS

| | | | |
|---|---|---|---|
| 5,704,922 A * | 1/1998 | Brown | A61M 5/31525 128/DIG. 1 |
| 8,922,367 B2 | 12/2014 | Denny et al. | |
| 9,179,260 B2 | 11/2015 | Ostrander et al. | |
| 9,402,954 B1 * | 8/2016 | Slevin | A61M 5/1723 |

(Continued)

*Primary Examiner* — Kami A Bosworth
(74) *Attorney, Agent, or Firm* — Armis IP Law, LLC

(57) ABSTRACT

An epinephrine auto-injector use activated device detects and responds to usage of the auto-injector. The resulting use activated device includes an actuator for manual generation of an injection force, as by a patient's hand, and a medicinal reservoir or vial for storing a quantity of medication for injection. A plunger is responsive to the actuator for displacing the medication in the medicinal reservoir, and a needle in fluidic communication with the medicinal reservoir defines a syringe for transporting the displaced medication through an aperture in a distal end of the needle. An electrical coupling, switch or sensor is responsive to movement of the actuator for initiating an alert signal. The alert signal is configured for transmission to a first responder in anticipation of an exigent response for further medical attention, in which the movement corresponds to plunger travel for dispensing the medication in the medicinal reservoir.

5 Claims, 12 Drawing Sheets

(56) References Cited

U.S. PATENT DOCUMENTS

| | | | |
|---|---|---|---|
| 2008/0021438 A1* | 1/2008 | Dacquay | A61F 9/0017 604/521 |
| 2011/0112474 A1* | 5/2011 | Bochenko | A61M 39/02 604/68 |
| 2011/0270214 A1* | 11/2011 | Jorgensen | G06F 19/00 604/500 |
| 2014/0200510 A1* | 7/2014 | Agard | A61M 5/3157 604/65 |
| 2015/0265828 A1* | 9/2015 | Colman | F16L 25/01 604/535 |
| 2015/0367080 A1* | 12/2015 | Draper | A61M 5/20 604/207 |
| 2015/0374907 A1* | 12/2015 | Morton | A61M 5/14546 604/111 |

\* cited by examiner

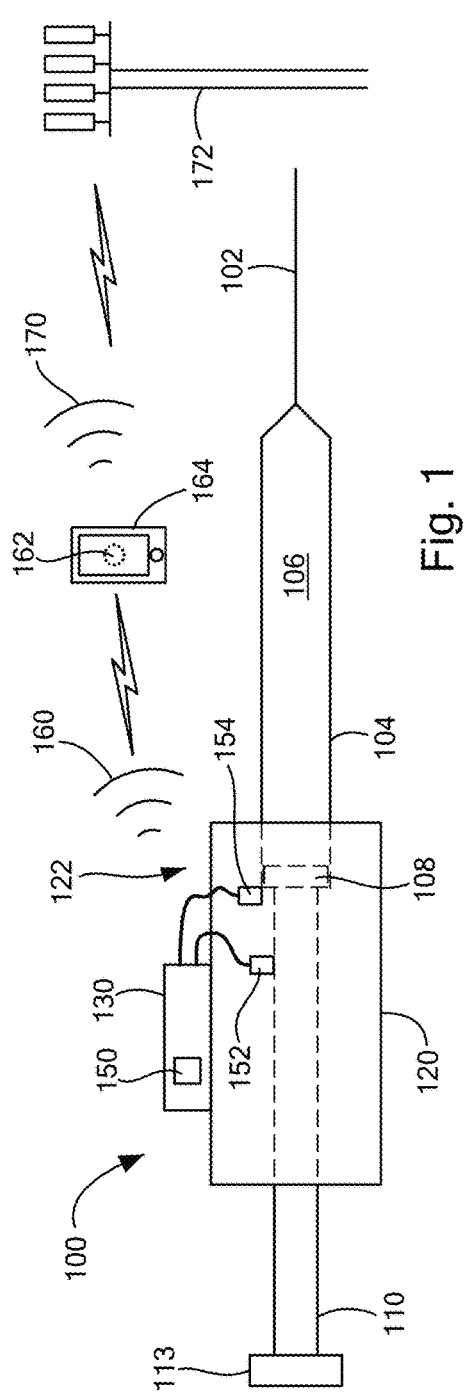
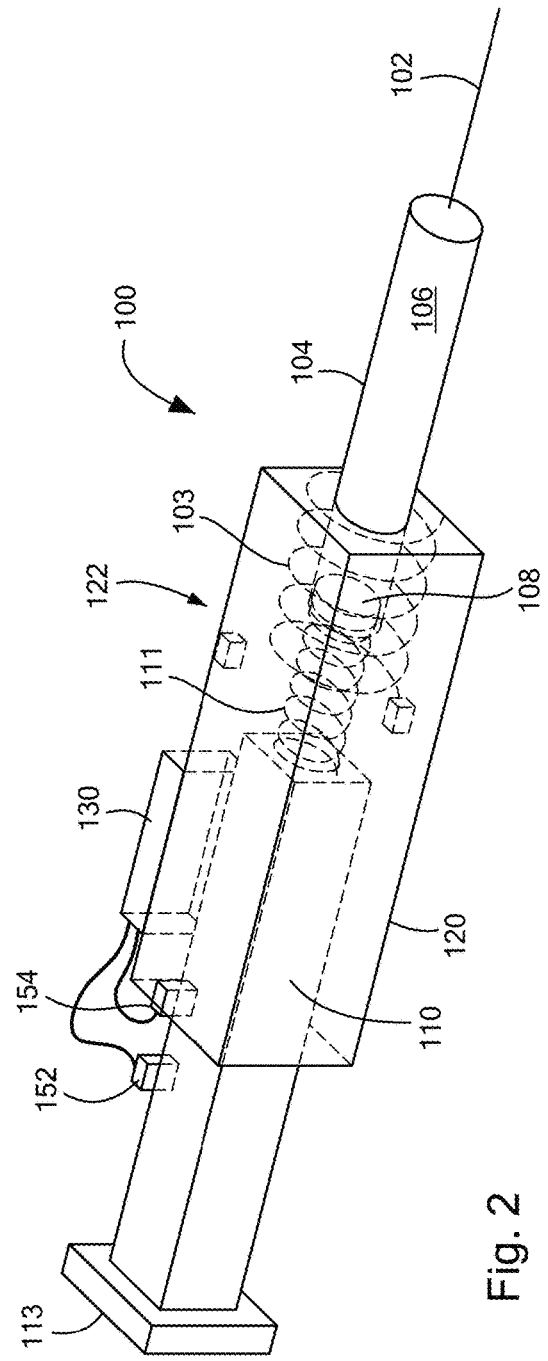

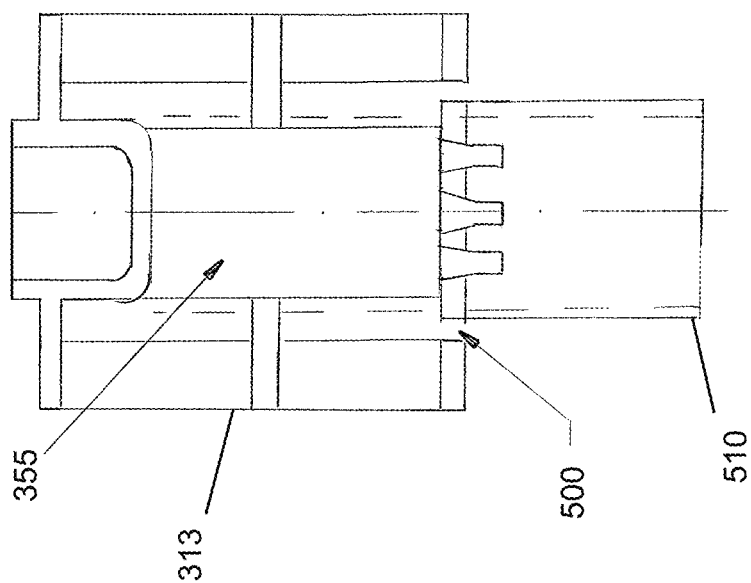

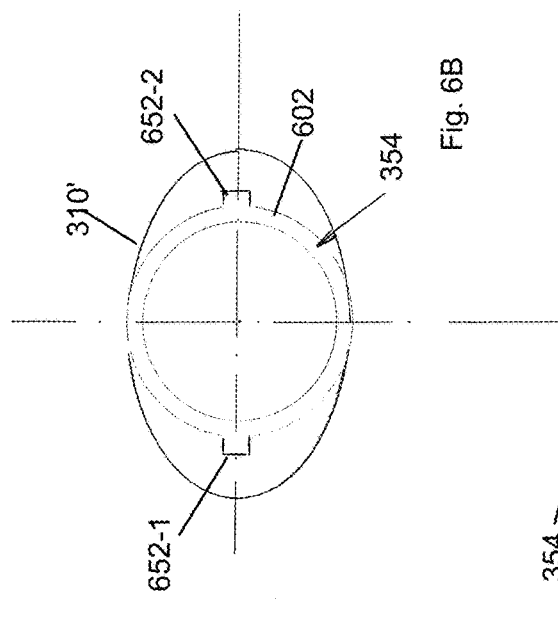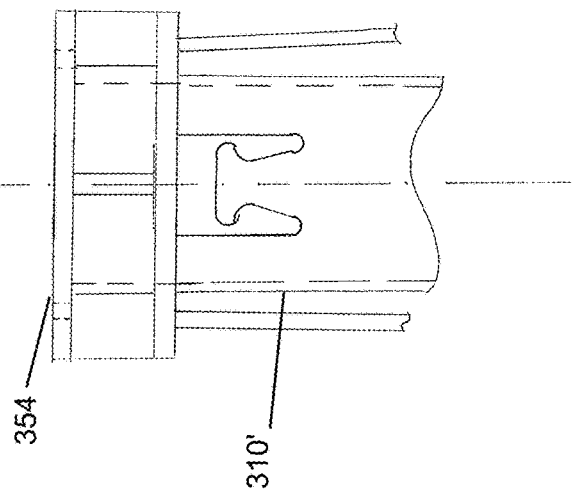

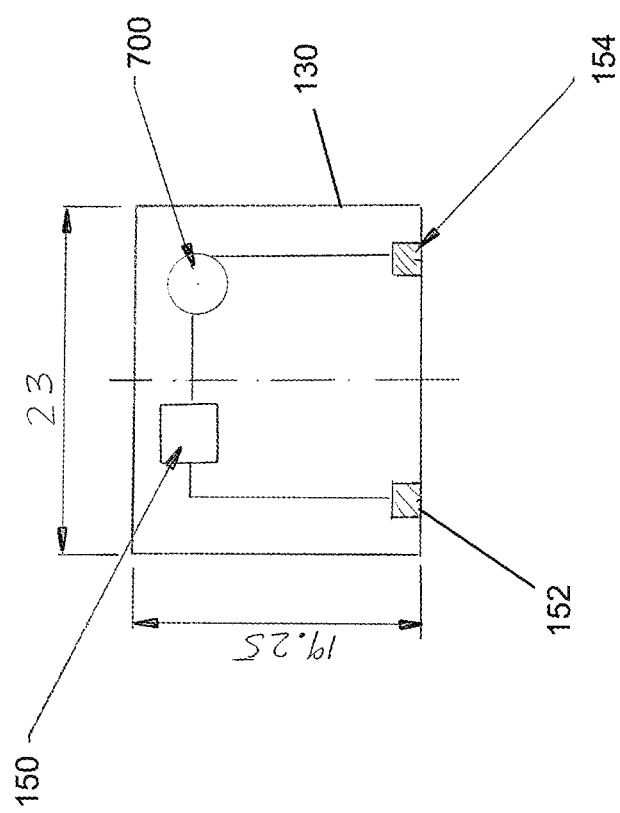

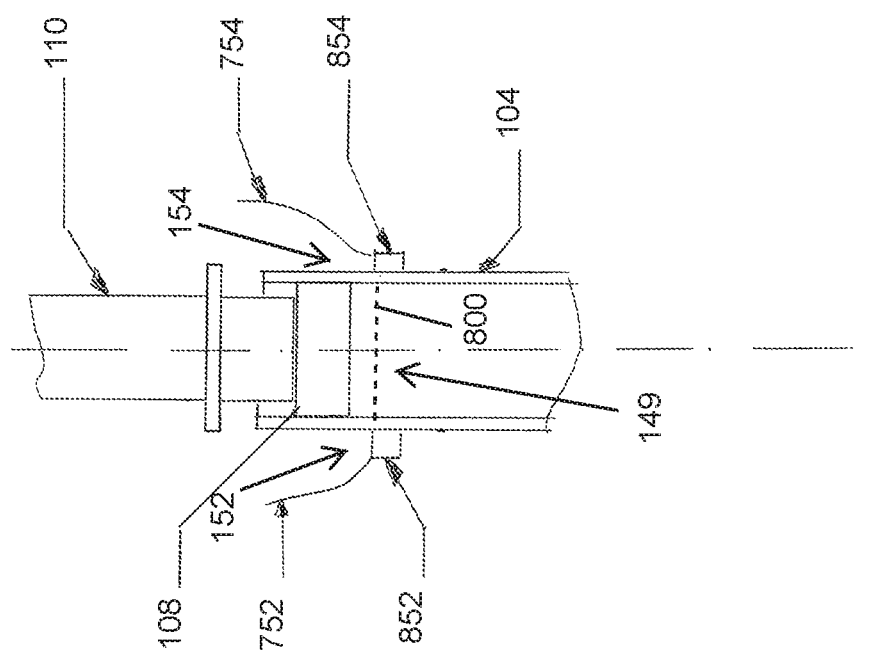

USE ACTIVATED EMERGENCY ALERT FOR A MEDICAL DEVICE

RELATED APPLICATIONS

This patent application claims the benefit under 35 U.S.C. § 119(e) of U.S. Provisional Patent App. No. 62/124,753, filed Jan. 2, 2015, entitled "USE ACTIVATED EMERGENCY ALERT SYSTEM FOR THE EPIPEN," incorporated herein by reference in entirety.

BACKGROUND

Anaphylaxis is a rapid and life-threatening allergic reaction. Allergic reactions from food and other stimuli have resulted in substantial efforts towards public awareness of the dangers of food allergies and the need to identify and isolate potential allergens in public or common areas. Many schools, for example, establish "nut free" tables or areas due to the high prevalence of nut allergies. Those with severe allergies can become afflicted with anaphylactic reactions when allergens are suddenly encountered.

An anaphylactic reaction can be triggered by allergens contained in food, medication, air, or delivered through insect stings. While many people manifest mild allergies to a variety of toxins, anaphylactic reactions result in rapidly progressing, life threatening symptoms. Symptoms can include a tightening of the airways, swollen throat, shock, rapid pulse, and dizziness or loss of consciousness. The reaction proceeds at an extremely fast pace and for those manifesting such an allergy, can be life-threatening within minutes of an allergen entering the human body.

A well known, short term treatment for an anaphylactic reaction is an injection of epinephrine, the drug of choice for treating a life-threatening allergic reaction from anaphylaxis.

SUMMARY

In the United States, an estimated 15 million people have severe allergies and are potentially susceptible to anaphylactic shock. Epinephrine auto-injectors are the preferential, portable self administered treatment option currently available. Auto-injector devices are designed to deliver a specific amount of epinephrine upon use to increase a window of time the victim of the allergic reaction has to seek medical attention. Epinephrine auto-injectors are available by prescription only and are only prescribed to people with severe allergies. Training provided to potential users can be condensed to two basic steps: inject, then call 911. Configurations disclosed below alert medical emergency responders automatically, removing one step from the procedure and therefore reducing the chances of human error.

The disclosed configurations combine an epinephrine auto-injector with technology that allows the use of smartphones or other personal computing devices connected to a communications network for initiating the 911 call. Combined with notification logic operable via an application (app) on the device, the smart epinephrine auto-injector will activate the computing device to transmit location information about the location of use to emergency response personnel. The incorporation of early detection and notification in conjunction with the remedial epinephrine dosage treatment ensures that appropriate primary care is available in a timely manner. In conventional approaches, early detection is in the hands of people who aren't always qualified to recognize it: the patient, family, and friends.

Configurations herein are based, in part, on the observation that portable, user activated emergency medical or medicinal devices often require exigent medical care thereafter to complement the treatment or injection provided by the medical device. Unfortunately, conventional approaches to portable, user activated self-treatment devices require proactive engagement of emergency personnel following use. Such proactive engagement, such as a call or transport to a medical facility, may not be readily achievable by a patient user who is still incapacitated, alone, and/or otherwise removed from competent assisters or medical facilities. A typical scenario may be illustrative. Epinephrine injections are often beneficial to patients with severe allergies, who may encounter allergens at any time. Medical devices are known which allow a patient user to carry an epinephrine dose for immediate injection by an afflicted user. A so-called "auto-injector," marketed commercially under the name EPI-PEN®, allows an afflicted patient to receive an epinephrine dose via self-injection to relieve the allergic reaction symptoms, which can include airway blockage that would otherwise result in asphyxiation.

However, such a remedial device may provide only short term relief, and more formal medical attention may be needed to fully treat the allergic reaction requiring the epinephrine dose. Accordingly, configurations herein substantially overcome the shortcomings of conventional injection devices by providing a use activated communication signal for alerting medical personnel to injection device deployment and requesting exigent care such as a 911 emergency response. The disclosed use-activated device includes a transmitter, response circuit and a switch or other electrical coupling triggered by injection or usage of the remedial device. A device app, running on the patient's cellphone or smartphone, is responsive to the transmitter for initiating a 911 call and transmitting the location of the patient for first responders.

In specific configurations disclosed herein, the use activated device is integrated or attached to an auto-injector for detecting and responding to usage of the auto-injector. The resulting use activated device includes an actuator for manual generation of an injection force, as by a patient's hand, and a medicinal reservoir or vial for storing a quantity of medication for injection. A plunger is responsive to the actuator for displacing the medication in the medicinal reservoir, and a needle in fluidic communication with the medicinal reservoir defines a syringe for transporting the displaced medication through an aperture in a distal end of the needle. An electrical coupling, switch or sensor is responsive to movement of the actuator for initiating an alert signal. The alert signal is configured for transmission to a first responder in anticipation of an exigent response for further medical attention, in which the movement corresponds to plunger travel for dispensing the medication in the medicinal reservoir. The alert signal may be in the form of a proximate signal to the user's cellphone or smartphone, where a receiving app combines with GPS (global positioning system) information for initiating a 911 call. Thus, the self-injection of epinephrine via the auto-injector results in a 911 call including the location of the patient for follow up response.

In an example configuration, the proximate signal issued by the injection device mounted transmitter is in the form of a BLUETOOTH®, WiFi or other short range transport medium. The bluetooth signal is receivable by a paired or default setting of the user's wireless communication device, and an application (app) already installed in conjunction with the response circuit retrieves the current GPS location along with identity information of the patient/user, and transmits this information in a 911 call for facilitating the exigent response.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

FIG. 1 is a context diagram of an injection device suitable for use with configurations herein;

FIG. 2 is a perspective view of an example auto-injector as in the context of FIG. 1;

FIG. 5 is a front elevation of the top stop of FIG. 3;

FIGS. 6A and 6B are front and top views of the syringe guide of FIG. 3;

FIG. 7 shows a schematic of the circuit board having the response circuit of FIG. 3;

FIG. 8 shows an alternate configuration having an optical coupling for triggering the response circuit of FIG. 3;

DETAILED DESCRIPTION

Figure 3:
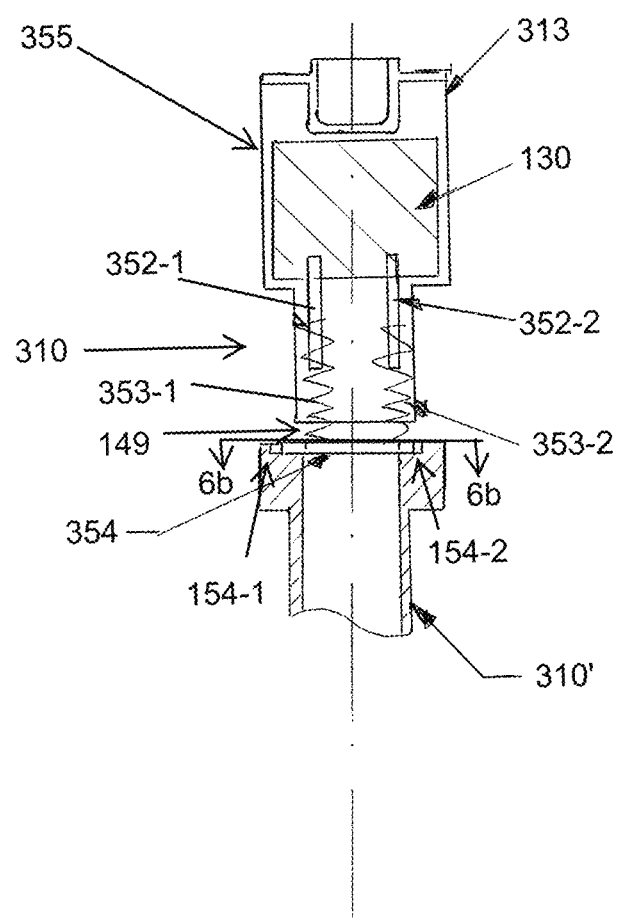
FIG. 3 is a side elevation of an integration or retrofit of an auto-injector with an activation coupling and response circuit as disclosed herein.

Depicted below is an example of the response circuit in conjunction with an auto-injector device for automatic initiation of a 911 call from the user's device upon detected usage of the auto-injector. A context view depicts certain elements of the disclosed approach with a syringe. Other configurations depict installation of the response circuit in conjunction with an auto-injector device, which includes additional elements for safeguarding the auto-injector from inadvertent or multiple uses. Additional safety or actuation features in conjunction with the injection apparatus do not affect operation of the response circuit, and may present additional activation points from which device use may be construed based, directly or indirectly, from travel of the syringe plunger.

There are a number epinephrine auto-injectors currently available. Typical auto-injectors perform a common basic function, delivering a specific amount of epinephrine to the patient when used properly. An epinephrine auto-injector is the only home treatment available to people with allergies and provides the highest chance of survival for the person going into anaphylactic shock. However, it is only a temporary solution to anaphylaxis, and professional medical assistance is generally required immediately after injection. Configurations discussed further below disclose an approach that can be adapted to any epinephrine auto-injector and is not specific to the EPI-PEN® brand or the pen shaped design.

Portable epinephrine injection devices, or "auto-injectors," typically feature a protective case that contains a spring loaded system containing a needle, vial, and plunger. Upon use, the spring system is compressed allowing the needle to protrude through a hole in the protective casing to enter the patient's body. A hard stop in the shape of a collar that exceeds the inner diameter of the vial on the plunger ensures that only the proper amount of epinephrine from the vial is injected. The spring mechanism retracts the needle back into the protective housing after use. A locking mechanism that engages after initial use prevents reuse of the auto-injector. The design of such auto-injectors is sophisticated in detail and has saved many lives since the device was introduced into the market. Most auto-injectors operate on the same basic principal of ensuring a measured injection of epinephrine to the user while preventing re-use and accidental injury through the needle prior to or after use.

Conventional approaches, such as that disclosed in U.S. Pat. No. 9,179,260, employ a circuit for tracking expiration of the medication in the device, but do not disclose an electrical coupling activated by actuator displacement for sending an alert signal to a cellphone app. The '260 approach requires communication between a medication vial, and a logic circuit for tracking and comparing dates, employing substantial electronic circuitry and logic for identifying and communicating an expiration event. In contrast, the disclosed approach employs a single switched circuit for activating an OTS (off the shelf) transmitter for communicating with a mobile device of the user, such as via a BLUETOOTH® communication.

FIG. 1 is a context diagram of an injection device suitable for use with configurations herein. Referring to FIG. 1, an injection device 100 such as a syringe or similar apparatus includes a needle 102, a medication repository or vial 104 containing the medication 106 to be injected, a plunger 108 adapted to be forced through the vial at close tolerances for forcing the medication through the needle 102, and an actuator or shaft 110 for providing force for disposing the plunger through the vial 104.

The injection device may include a housing 120 encapsulating at least portions of the vial 104 and shaft 110, for example to implement post-usage safety mechanisms to retract the needle 102 and ensure single use operation, discussed further below. A circuit board 130 attached to a side 122 of the housing 120 includes a response circuit 150. A first contact element 152 and a second contact element 154 are disposed at complementary positions on the shaft 110 and vial 104 or housing 120. Movement of the shaft 110 disposing the plunger 108 sufficient to displace at least a dosage of medication 106 causes engagement of the contact elements 152, 154 to close a circuit for triggering the alert signal 160. Upon detecting the contact elements 152, 154 closing, the response circuit 150 initiates the alert signal 160 via Bluetooth or other wireless format for reception by a monitor application (app) 162 on the patient's wireless device 164 (e.g. smartphone, cellphone, etc.) In particular configurations, the alert signal 160 includes a message containing an identity of the user for indexing into a database of medical history for enabling first responders to access information for strategic medical response.

The app 162 gathers several data items, including GPS (Global Positioning System) coordinates indicative of the device location, identity of the user, and an indication of the circumstances, such as auto-injector usage, and generates a 911 call message 170 via a local cell tower 172. Various manners of engagement of the contact elements 152, 154 may be detected by the response circuit, such as conductive, optical or proximity sensing, or even disconnection of a closed circuit (i.e. alert signal triggered by contact elements 152, 154 opening).

FIG. 2 is a perspective view of an example auto-injector as in the context of FIG. 1. Any suitable injection device such as an auto-injector can be integrated, retrofitted or designed with the electric coupling, response circuit and other elements as disclosed herein. Referring to FIG. 2, a housing 120 contains the plunger 108, and the actuator or shaft 110 is slidably disposed within a bore in the housing 120. The circuit board 130 is affixed to the housing 120 at a side 122, such that the circuit board is connected to the electrical coupling for receiving the alert signal 160.

While the housing is generally not needed for performing a syringe operation, consumer directed auto-injector implementations typically include a housing for providing protection against accidental discharge and ensuring single usage of adequate medicinal discharge. Configurations herein employ a switching element on the housing, in which the housing retains a resilient coupling such as a spring between the actuator and the plunger, and the housing is configured to retract to an unusable position subsequent to a first usage to avoid unintended usage. The electrical coupling initiates the alert signal based on travel of the actuator within the housing.

In operation, the housing 120 encapsulates a spring loaded mechanism for disposing the plunger 108 and for retracting the needle 102 inside the housing 120 following use. The shaft 110 compresses an injection spring 111 for advancing the plunger 108 in a controlled manner. An enlarged region 113 defines a handle for receiving a manual activation force from the user/patient. Following injection and delivery of the medication 106 in the vial 104, a retraction spring 103 forces the needle 102 inside the housing 120 and conceals the needle 102 from further usage. For example, the contact element 152 may be disposed on a distal end of the shaft 110 for engaging the contact element 154 at the top of the housing 154. The contact elements 152, 154 may be disposed in any suitable location, as now described with respect to FIGS. 3-13 below.

FIG. 3 is a side elevation of an integration or retrofit of an auto-injector with an activation coupling and response circuit as disclosed herein. Referring to FIGS. 1-3 and 5, an actuator 310 has a top stop 313 enlarged for receiving an actuation force from a patient during use of the auto-injector for the epinephrine dose. The circuit board 130 attaches to a side of the top stop 313 on a mounting surface 355 that is leveled, flattened or machined for ease of attachment. A pair of contact spring guides 352-1, 352-2 (352 generally) connect to the circuit board 150 and engage respective contact springs 353-1, 353-2 (353 generally). Upon use of the auto injector a spring displaces a top spring guide 510 which releases the contact springs 353. The top spring guide 510 is assembled in the top stop 313. The contact spring guides 352, the contact springs 353, and a conductive collar 354 surrounding a circumference of the syringe guide 310' form a closed circuit. The conductive collar 354 therefore defines the second contact element 154.

In the configuration of FIG. 3, an electrical coupling 149 is formed by the contact springs 353 and guides 352. The guides 352 define the first contact element 152 for completing the actuation circuit and triggering the response circuit 150 to transmit the alert signal 160. It should be emphasized that the electrical coupling 149 is achieved by the force applied by a patient/user during normal usage, such that response circuit 150 invocation is automatically performed during use. Typically, the electrical coupling 149 closes to initiate transmission of the alert signal, however circuit opening could also initiate the alert signal 160. In operation, the top spring guide 510 integrated in the top stop 313 acts as a secondary actuator and drives the plunger either directly or indirectly via the injection spring 111. The contact springs 353, guides 352 and conductive collar 354 therefore define opposed contacts. Thus, the conductive collar 354 is disposed around the bore in the syringe guide 310', and a connection from the circuit board 130 to the opposed contacts forms the electrical coupling 149 defined by the opposed contacts (contact guides 352) and the conductive collar 354. The opposed contacts are adapted to electrically connect to the conductive collar 354 upon disposing the actuator through the bore. The opposed contacts are adapted to electrically connect to the conductive collar 354 upon use of the auto injector. The opposed contacts extend along a longitudinal side of the top stop 313 and the conductive collar 354 circularly surrounds an opening of the bore, such that the opposed contacts are adapted to engage the conductive collar upon travel of the top spring guide 510 for disposing the plunger 108.

Figure 4:
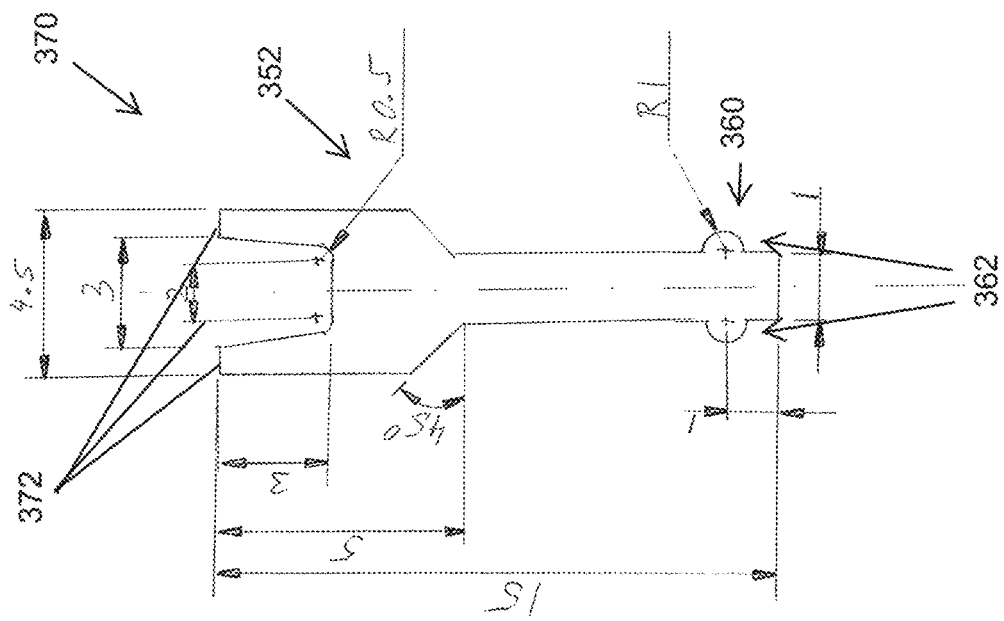
FIG. 4 is a front elevation of the spring guide of FIG. 3.

FIG. 4 is a front elevation of the spring guide 352 of FIG. 3. Referring to FIGS. 3 and 4, the spring guide 352 is defined by an elongated, conductive structure having an enlarged region 360. The enlarged region 360 includes protrusions 362 for engaging the springs 353. An opposed end 370 includes branched members 372 for facilitating connections to the circuit board 130 and attachment to the top stop 313.

FIG. 5 is a front elevation of the top stop of FIG. 3. Referring to FIGS. 3-5, the top stop 313 is formed or modified to define the flat recess 355 for receiving and mounting the circuit board 130. The spring contact guides 352 engage a receptacle 500 on the top stop 313 to secure the spring contact guides 352 for movement with the top stop upon device activation. As described above with respect to FIG. 3, the top spring guide 510 is displaced during auto injector use and engages the springs 353.

FIGS. 6A and 6B are front and top views of the syringe guide of FIG. 3. Referring to FIGS. 3, 6A and 6B, the syringe guide 310' operates generally to contain and direct the injection spring 111 and retraction spring 103 for directing the plunger 108 and withdrawing the needle 102 into the housing 120 after use, respectively. The springs 103, 111 and syringe guide 310 are not required for implementing the contact points 152, 154 and response circuit 150, however are beneficial to overall device operation. The conductive collar 354 is circumferentially disposed around a shaft bore 600, and closes the electrical coupling between the contact points 152, 154 in response to the top spring guide 510. The conductive collar 354 lies in a recess 602, and has contact tabs 652-1, 652-2 extending outward for engaging the contact spring guides 352-1, 352-2, respectively.

FIG. 7 shows a schematic of the circuit board 130 having the response circuit 150 of FIG. 3. The circuit board 130 is sized for reengagement or attachment with the flat recess 355 on the top stop 313, however any suitable mounting location may be employed. Conductive leads 852 and 854 connect to the contact points 152 and 154, respectively, for defining the electrical coupling 149.

FIG. 8 shows an alternate configuration having an optical coupling for triggering the response circuit 150 of FIG. 3. Epinephrine, the medicine for anaphylaxis, is a clear substance and thus a beam of light can pass through the glass vial while the adrenaline is contained within. A small emitter and receiver are attached to the vial. Electrical leads are guided within the assembly from the emitter and receiver to the circuit board. Upon use of the auto-injector the plunger is displaced, and the movement of the plunger from its initial position to its end position, determined by a dead stop, breaks the light beam. Once the beam is broken, the Bluetooth circuit is activated, establishing a connection with the smartphone application.

Referring to FIGS. 3, 7 and 8, the electrical coupling 149 is defined by an optical emitter 852 and receiver 854 disposed at opposed sides of the vial 104. The vial 104 defining the medicinal reservoir typically comprises an optically clear material, and the plunger 108 is configured to engage an interior of the vial 104 for forcing the medication through the needle 102. An optical coupling is formed across opposed sides of the vial 104, such that the optical coupling is responsive to interruption of an optical signal across the vial resulting from plunger 108 travel. Since the vial is typically glass or plastic, an optical signal may be passed between, as shown by dotted line 800. The emitter 852 may be any suitable light source, such as an LED (light emitting diode) or infrared source, and the receiver of a complementary element. Travel of the plunger 108 interrupts the optical signal 800 during use of the injection device 100 for initiating the response circuit 150.

Figure 9:
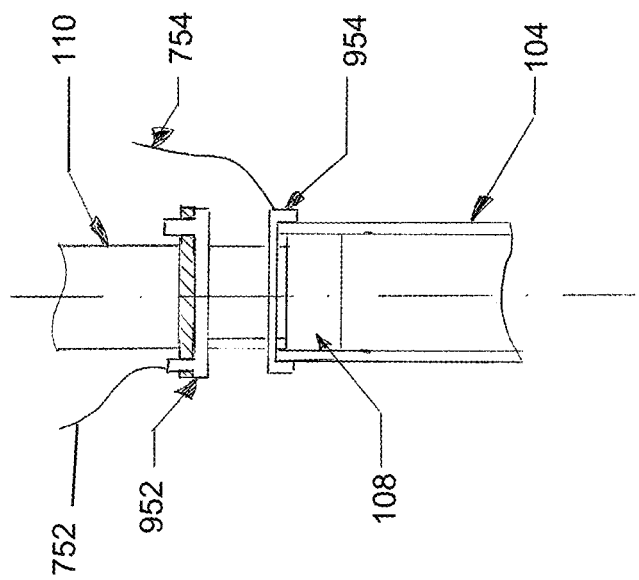
FIG. 9 shows a configuration having a contact ring on the vial for triggering the response circuit of FIG. 3.

FIG. 9 shows a configuration having a contact ring on the vial for triggering the response circuit 150 of FIG. 3. The plunger 108 attaches to the actuator, or shaft 110, in which the actuator has a stop collar around a circumference, and the stop collar is configured to engage the medicinal reservoir for limiting travel of the plunger 108 to limit a delivered quantity of medication. A plurality of contacts attach to the stop collar (typically 2), such that each of the contacts connects to the circuit board. A contact ring is disposed around the top of the medicinal reservoir, such that the contact ring is configured to engage the plurality of the contacts for closing the electrical coupling 149 upon movement of the plunger 108 into the medicinal reservoir.

A conductive ring is used as the dead stop for the syringe plunger. The conductive ring is connected to the circuit board via a lead guided within the assembly. This ring functions as dead stop for the plunger and one part of the switching mechanism, which activates the Bluetooth circuit. The second part of the switch is formed by a ferrule that is located on top of the vial. The vial contact cap is connected to the circuit board through a lead guided through the auto-injector assembly. When the auto-injector is used, the plunger is displaced, forcing the dead stop ring into contact with the vial cap. The contact activates the Bluetooth circuit.

Referring to FIGS. 3, 7 and 9, a conductive contact ring 952 encircles the circumference of the shaft 110 and connected to lead 752 to define the first contact point 152. A vial contact ring 954 attaches to a top circumference of the vial 104 for defining the second contact point, and establishing the electrical coupling 149 upon shaft 110 travel toward the vial 104 for displacing the plunger 108.

Figure 10:
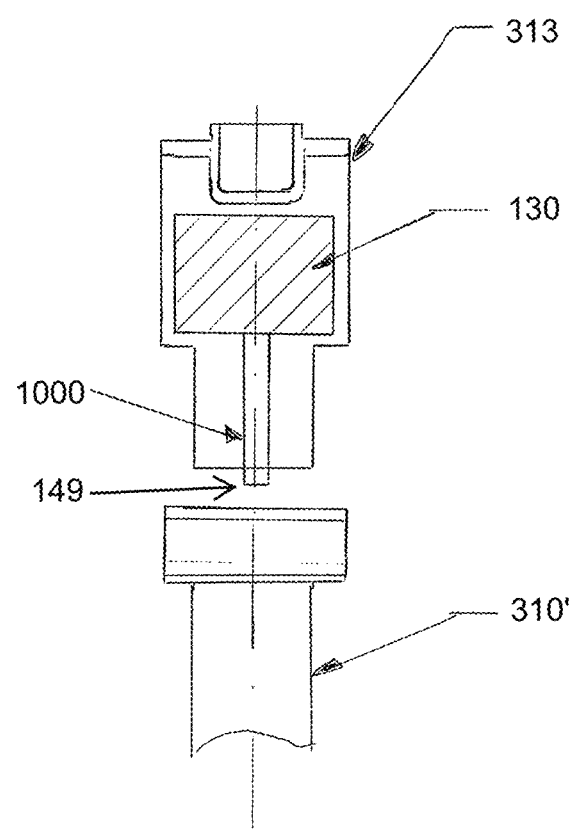
FIG. 10 shows a configuration having a proximity sensor in the syringe guide of FIG. 3.

FIG. 10 shows a configuration having a proximity sensor in the syringe guide 310' of FIG. 3. In this configuration, a proximity sensor is in communication with the actuator, such that the proximity sensor is configured to sense the actuator approaching the housing. The proximity sensor couples to the circuit board 130 for defining the electrical coupling 149. The proximity sensor is connected between the circuit board and the top stop. The proximity sensor may use any number of functional designs, including light or magnetic field detection. When the auto-injector is used, the complete assembly is compressed and the syringe guide will come into close proximity with the top stop. A light emitting proximity sensor can detect this closeness based on the light reflecting from the top surface of the syringe guide. Once the proximity is detected, the Bluetooth circuit is activated. Using an LED as the light emitter allows the sensor to perform a dual function. The LED can be lit in green, indicating that the auto-injector is ready for use. Once the auto-injector has been used, the LED color changes to red.

Referring to FIGS. 3 and 10, a proximity sensor 1000 extends from the circuit board 150, for engaging and activating a proximity receptor 1002 on the syringe guide 310'. Any suitable proximity sensor 1000 may be employed, such as a Hall effect sensor, for inducing an electric signal in the proximity receptor 1002 for establishing the electrical coupling 149.

Figure 11:
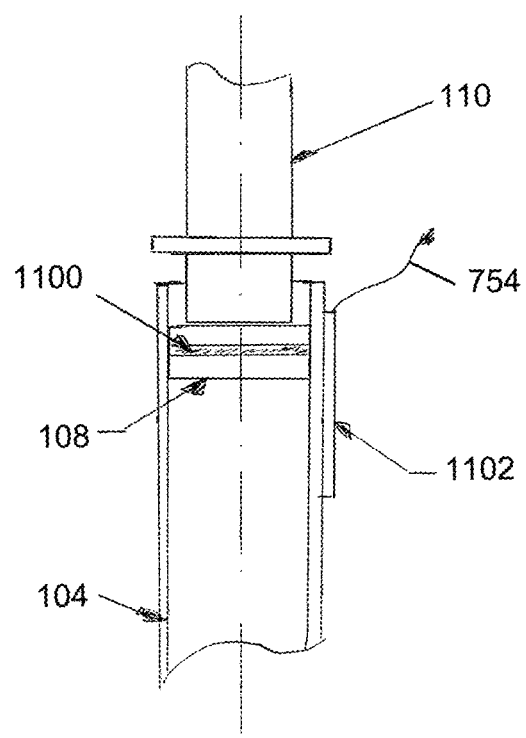
FIG. 11 shows an inductive coupling for detecting movement of the plunger of FIG. 3.

FIG. 11 shows an inductive coupling for detecting movement of the plunger of FIG. 3. An inductive ring is disposed in the plunger, and an inductive sensor on an exterior side of the medicinal reservoir is responsive to movement of the inductive ring within the medicinal reservoir resulting from plunger movement. Referring to FIGS. 3 and 11, an inductive stimuli is embedded in the plunger 108, and activates an inductive sensor 1102. The inductive coupling may be, for example, a metal insert or other implant suitable for inducing an electrical signal in the inductive sensor 1102 for establishing the electrical coupling 149. At least one of the leads 754 connects to the inductive sensor, and the other contact point 152 may be established simply by a ground voltage reference.

Figure 12:
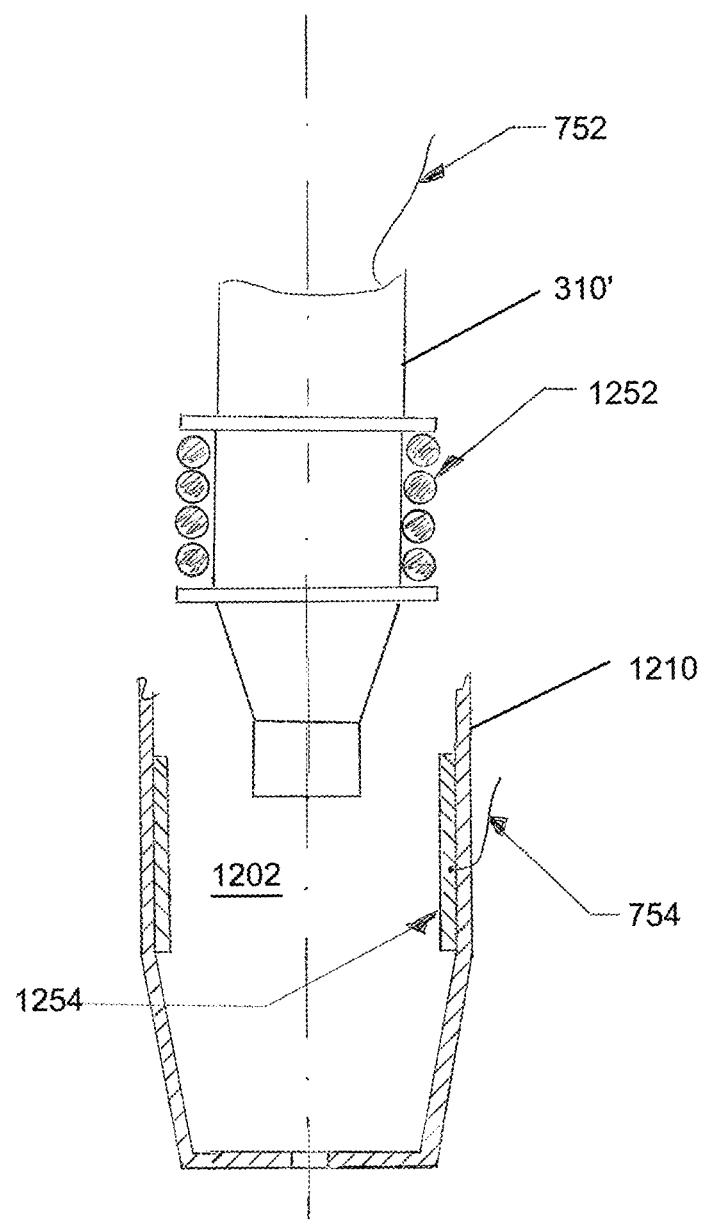
FIG. 12 shows a conductive coil coupling for triggering the response circuit of FIG. 3.

FIG. 12 shows a conductive coil coupling for triggering the response circuit of FIG. 3. Referring to FIGS. 3 and 12, a conductive sleeve surrounds an interior of the bore, and a conductive coil 1252 wraps around the actuator. The conductive coil 1252 is adapted to disengage the conductive sleeve 1254 upon travel of the actuator through the bore, such that the conductive coil and conductive sleeve 1254 interrupt connection to the circuit board 130 and are configured to open the electrical coupling 149 upon travel of the conductive coil through the conductive sleeve. Referring to FIGS. 3 and 12, a conductive coil 1252 surrounds at least a portion of the syringe guide 310', and establishes the first contact point 152. A syringe guard 1210 includes a conductive sleeve 1254 for defining the second contact point 154, which is disposed around a receptacle 1202 in the syringe guard 1210 for disengaging the conductive coil 1252 as the syringe guard 1210 is displaced upon auto-injector use. Alternative configurations could locate the coil 1252 and sleeve 1254 such that an open circuit defines an idle position and closure of the electrical coupling 149 demarcates use.

Figure 13A:
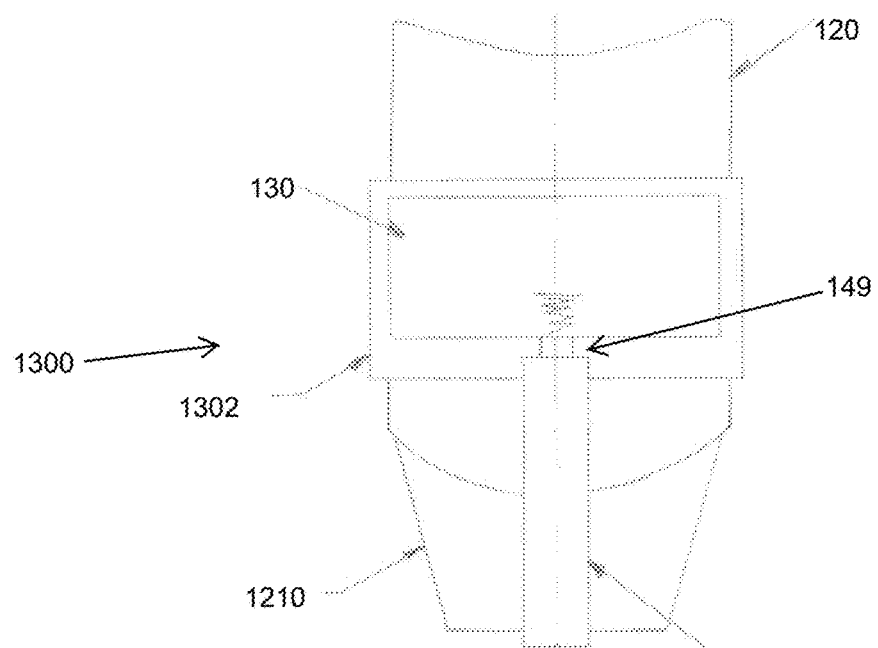
FIGS. 13A and 13B show an attachment interface for retroactive fitting of the circuit board for establishing the electrical coupling on a preexisting device.
Figure 13B:
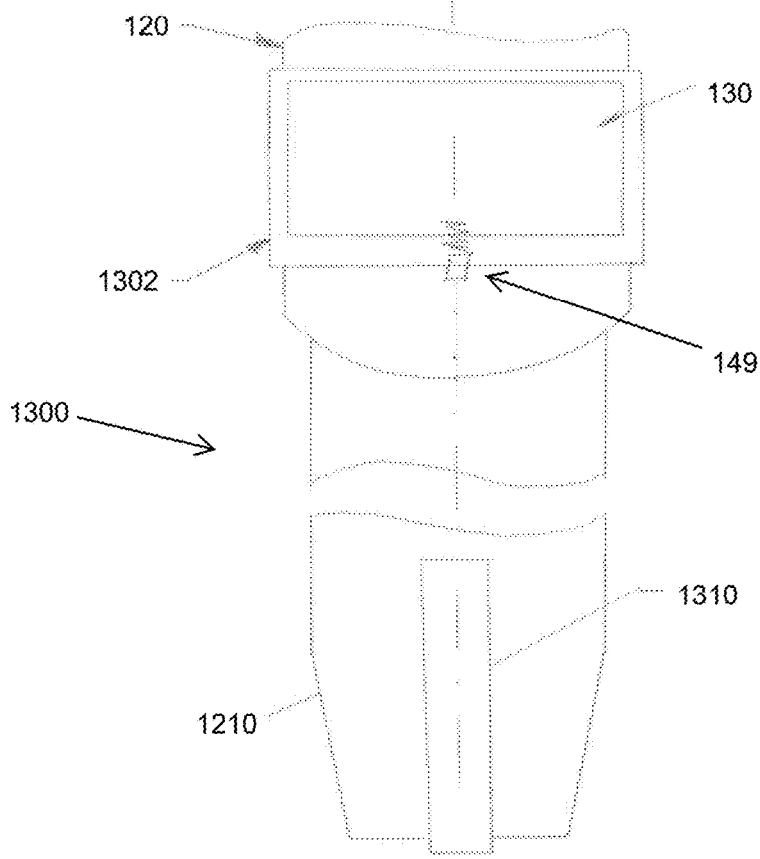

FIGS. 13A and 13B show an attachment interface for retroactive fitting of the circuit board 130 for establishing the electrical coupling on a preexisting device. Referring to FIGS. 3 and 13A & B, in the approach depicted in FIGS. 13A & B, the mechanism to allow the use of the auto-injector to notify emergency services is attached to the auto-injector 100 rather than integrated into the device. The external notification device 1300 may be attached to the auto-injector 100 by any suitable means, such as tape, adhesive, hook-and-loop (e.g. VELCRO®) or other means that forms a connection between the housing 120 and the circuit board 130 for securing the circuit board 130 from moving when the auto-injector is used.

In the configuration of FIGS. 13A and 13B, a trigger mechanism for establishing the electrical coupling 149 to initiate the notification may have different embodiments. In a particular example implementation, a trigger component 1310 is attached to a bottom of the syringe guard 1210 that extends from the housing 120 after the auto-injector has been used. An attachable bracket 1302 secures the circuit board 130, and may resiliently wrap around or be otherwise adhered to the housing 120 or syringe guard 1210 as space permits. While in the initial position, this trigger component 1310 keeps the electrical coupling 149 on the circuit board 130 open. When the auto-injector is used, the syringe guard 1210 separates from the housing 120 such that the trigger component 1310 is pulled out of the notification assembly, as shown in FIG. 13B, and the electrical coupling 149 is closed to notify emergency services, such as by removing a separator from between spring loaded or biased contacts. Alternatively, the unactivated position could be defined by the electrical coupling 149 being closed, and opening of the circuit establishes the alert signal 160.

Another alternate configuration for the external attachment is to use a sensor that detects the motion of the syringe guard 1210 when it is released. This can be accomplished via light, using an LED and a sensor that detects the light scatter, similar to the earlier configurations. After expansion to the used position, the light will scatter differently as parts within the auto-injector will have moved inside the housing 120.

A mechanical switch implementation may also be employed. In this configuration, during assembly of the externally attached notification device 1300, the housing of the auto-injector 100 would be pierced in a specific location. A trigger mechanism would penetrate into the auto-injector. When the syringe guard 1210 moves after use of the auto-injector the trigger would break or deform and thus signal a state change. This detection would trigger the emergency services notification system. In an alternate configuration, an expiration counter may be disposed on the circuit board, wherein a closed electrical coupling defines an unactivated alert signal based on an idle state of the medication injection device. The expiration counter is configured to render a visual expiration signal indicative of aging medication, such as illuminating a different colored LED, in which the alert signal is based on an opening of the electrical coupling.

It will be appreciated by those skilled in the art that alternate configurations of the disclosed invention include a multiprogramming or multiprocessing computerized device such as a workstation, handheld or laptop computer or dedicated computing device or the like configured with software and/or circuitry (e.g., a processor as summarized above) to process any or all of the method operations disclosed herein as embodiments of the invention. Still other embodiments of the invention include software programs such as a Java Virtual Machine and/or an operating system that can operate alone or in conjunction with each other with a multiprocessing computerized device to perform the method embodiment steps and operations summarized above and disclosed in detail below. One such embodiment comprises a computer program product that has a computer-readable storage medium including computer program logic encoded thereon that, when performed in a multiprocessing computerized device having a coupling of a memory and a processor, programs the processor to perform the operations disclosed herein as embodiments of the invention to carry out data access requests. Such arrangements of the invention are typically provided as software, code and/or other data (e.g., data structures) arranged or encoded on a non-transitory computer readable storage medium such as an optical medium (e.g., CD-ROM), floppy or hard disk or other medium such as firmware or microcode in one or more ROM, RAM or PROM chips, field programmable gate arrays (FPGAs) or as an Application Specific Integrated Circuit (ASIC). The software or firmware or other such configurations can be installed onto the computerized device (e.g., during operating system execution or during environment installation) to cause the computerized device to perform the techniques explained herein as embodiments of the invention.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A medication injection device, comprising:
an actuator configured for direct engagement by a user for manual generation of an injection force;
a medicinal reservoir for storing a quantity of medication for injection;
a plunger responsive to the actuator for displacing the medication in the medicinal reservoir;
a housing containing the plunger, the actuator slidably disposed within a bore in the housing;
a needle in fluidic communication with the medicinal reservoir for transporting the displaced medication through an aperture in a distal end of the needle;
an electrical coupling responsive to movement of the actuator for initiating an alert signal upon closure of the electrical coupling, the alert signal configured for transmission to a first responder in anticipation of an exigent response for further medical attention, the movement corresponding to plunger travel for dispensing the medication in the medicinal reservoir,
the electrical coupling defined by opposed contacts attached to the actuator and a circular conductor defined by the bore, the opposed contacts adapted to electrically connect to the circular conductor upon disposing the actuator through the bore;
a circuit board affixed to the housing for initiating the alert signal;
and
a connection from the circuit board to the opposed contacts.

2. The device of claim 1 wherein the opposed contacts extend along a longitudinal side of the actuator and the conductive collar circularly surrounds an opening of the bore, the opposed contacts adapted to engage the conductive collar upon travel of the actuator for disposing the plunger.

3. The device of claim 1 further comprising a switching element disposed on the housing, the housing retaining a resilient coupling between the actuator and the plunger.

4. The device of claim 1 wherein the alert signal includes a message containing an identity of the user for indexing into a database of medical history for enabling first responders to access information for strategic medical response.

5. The device of claim 1 further comprising:
a conductive sleeve around an interior of the bore defining the circular conductor.

* * * * *